United States Patent [19]
Haslbeck

[11] Patent Number: 5,711,035
[45] Date of Patent: Jan. 27, 1998

[54] MULTI-SPORT EYE PROTECTOR

[75] Inventor: Joseph Haslbeck, West Vancouver, Canada

[73] Assignee: Sharp Plastics Manufacturing Ltd., Canada

[21] Appl. No.: 610,244

[22] Filed: Mar. 4, 1996

[51] Int. Cl.$^6$ .................................................. A61F 9/02
[52] U.S. Cl. ................................. 2/436; 2/442; 2/446
[58] Field of Search .............................. 2/426, 431, 432, 2/435, 436, 437, 439, 440, 441, 445, 446, 447, 448, 450, 452, 454, 442

[56] References Cited

U.S. PATENT DOCUMENTS

| | | | |
|---|---|---|---|
| 1,258,097 | 3/1918 | Day | 2/439 |
| 2,773,260 | 12/1956 | Hirschmann | 2/441 |
| 2,877,462 | 3/1959 | Moeller | 2/440 |
| 3,945,044 | 3/1976 | McGee et al. | 2/436 |
| 4,067,069 | 1/1978 | Slosek et al. | 2/441 |
| 4,447,914 | 5/1984 | Jannard | 2/432 |

FOREIGN PATENT DOCUMENTS 212471  3/1941  Switzerland ........................ 2/426

OTHER PUBLICATIONS

Reebok Eyewear (Publication Date prior to 4 Mar. 1995).
Briko Sporteyes (Publication Date prior to 4 Mar. 1995).

*Primary Examiner*—Michael A. Neas
*Attorney, Agent, or Firm*—Bull, Housser & Tupper

[57] ABSTRACT

Eye goggles for use in different sporting activities to protect the eyes against harsh light and possible impact injury. The goggles comprise a goggles frame having a pair of eyepiece frames interconnected by a nosepiece, a pair of eyepiece lenses, and a goggles retainer to retain the goggles against the wearer's face. Each eyepiece frame has elongated and spaced apart inner and outer support elements in which the inner support elements are locatable between a wearer's face and an adjacent outer support element. The support elements are spaced apart by a plurality of relatively short spacer elements and extend in generally similar directions to define upper and lower edge portions of each eyepiece frame. The spacer elements are spaced apart along lengths of the support elements to provide ventilation openings located between the support elements and spacer elements. Each lens is connected to a respective outer support element of each eyepiece frame to retain the lens within the frame so that the ventilation openings are exposed between the lens and the wearer's face.

20 Claims, 4 Drawing Sheets

MULTI-SPORT EYE PROTECTOR

BACKGROUND OF THE INVENTION

The invention relates to an eye protector or goggles for use when participating in a wide variety of activities to protect the eyes from harsh light and/or impact injury.

There are many types of eye protectors or goggles which protect the eyes from harsh light, for example ski goggles, and also goggles to protect the eye from impact injury, for example racquetball or squash goggles. Usually, goggles which are suitable for one activity are unsuitable for another, and thus participants of many activities have different goggles for each of their different activities.

Each different activity requiring goggles tends to dictate the design and construction of each type of goggle. For example, sun glasses or ski goggles to protect the eyes from harsh light are usually not subjected to much force and are commonly constructed from relatively lightweight materials. Such materials tend to be flexible and do not offer much resistance to impact, and thus sun glasses or ski goggles do not protect the eyes adequately from impact injury and are not used in other sports where eye impact is likely. Also, ski goggles have a resiliently padded frame supporting a wrap-around single curvature lens, which is supported essentially continuously around its periphery by the wearer's face. The frame is relatively flexible to conform to the wearer's face and the frame relies mostly on support from the wearer's face for strength. Any impact in the lens tends to result in gross deflection of the lens and frame, and thus ski goggles usually do not provide adequate support against impact injury.

Racquetball or squash goggles usually do not offer any protection against harsh light, and commonly, due to their design for strength for impact injury protection, are relatively heavy and not particularly comfortable for long periods of use. It has been found that a person will often neglect to wear goggles that are heavy or uncomfortable, thus increasing the risk of eye injury, particularly in sports where eye injury is to be expected, such as squash or racquetball. Because goggles that are relatively heavy and uncomfortable to wear are less likely to be worn than more convenient goggles, it is important that goggles should be light and comfortable.

Also, contact of the padded frame of the ski goggles with the face tends to limit ventilation, thus aggravating a tendency of the lens to "fog", i.e. collect condensation from perspiration during heavy exertion of the wearer. Sun glasses have lenses which are usually well spaced from the face which reduces fogging, but the lenses are usually supported on relatively weak and/or flexible frames which also provide poor protection against impact. Lenses which are well spaced from the face offer little protection against light entering the eyes from the side or from beneath and thus are not very effective for eye protection in harsh lighting conditions as found on snow.

Many types of eye protectors or goggles are provided with ventilation openings to reduce fogging of the lens. While ski goggles commonly have ventilation openings provided along upper and lower edges of the goggles, such openings tend to weaken the goggles thus further reducing any impact protection such goggles provide.

Multi-sport eye glasses or goggles are known, and commonly use a "wrap-around", single curvature lens which provides protection against light entering from the side and sometimes from beneath. A wrap-around lens is usually spaced some distance from the wearer's face to facilitate ventilation and side support frames are often eliminated to improve peripheral vision. Such glasses are normally supported on the face using conventional arms which engage the side of the head and/or the ears, and, because of their lightness, and the manner in which they are retained on the wearer's face, such glasses usually do not provide adequate protection against impact.

SUMMARY OF THE INVENTION

The invention reduces the difficulties and disadvantages of the prior art by providing an eye protector for use with different activities which has the advantage of providing a relatively stiff frame which is also additionally supported by contact with the wearer's face, and yet is provided with peripheral ventilation openings to reduce fogging of the lens. In addition, the lenses are generally spherical to provide a stiff barrier for additional protection against impact, while concurrently improving optical quality of the lens. The eye protector preferably has a one-piece or integral goggles frame which is designed to provide a relatively high strength-to-weight ratio, and thus for their weight the goggles are very strong and thus can be worn with negligible inconvenience to the wearer. The frame provides additional protection against eye injury should a lens be inadvertently displaced inwardly from the frame towards the eye. For convenience, the eye protector can be supported on the wearer's head using conventional spectacle arms which engage the head adjacent the ears, or alternatively a resilient band which passes around the head.

Eye goggles according to the invention comprise a goggles frame having a pair of eyepiece frames interconnected together by a nose piece, a pair of eyepiece lenses, and the goggles retainer. Each eyepiece frame has elongated and spaced apart inner and outer support elements, the inner support elements and being locatable between a wearer's face and an adjacent outer support element. The support elements are spaced apart by a plurality of relatively short spacer elements and extend in generally similar directions to define upper and lower edge portions of each eyepiece frame. The spacer elements are spaced apart along length of the support elements to provide a plurality of ventilation openings located between the support elements and the spacer elements. Each eyepiece lens is connected to a respective outer support element of each eyepiece frame to retain the lens within the frame. In this way, the ventilation openings are exposed between the lens and the wearer's face. The goggles retainer cooperates with the eyepiece frames to retain the goggles against the wearer's face.

Preferably, each outer support element has a groove therein to receive an edge of the eyepiece lens. Also, each outer support element has a thickness greater than thickness of each inner support element to provide additional thickness for the groove to receive the eyepiece lens. Also, each inner support element has width greater than width of the outer support element to provide a greater bearing area against the wearer's face and additional safety for the wearer's eye.

In one embodiment, the nose piece has a hinge portion extending therealong, the hinge portion being a relatively narrow strip having a thickness less than thickness of surrounding portions of the goggles frame and extending between the eyepiece frames. The hinge portion facilities slight bending between the eyepiece frames to accommodate variations in shapes of faces of different wearers.

Alternative eye goggles according to the invention comprises a goggles frame having a single eyepiece frame of elongated and spaced apart inner and outer support elements. The inner support element is locatable between a wearer's face and the outer support element. The support elements are spaced apart by a plurality of relatively short spacer elements and extend in generally similar directions to define upper and lower edge portions of the eyepiece frame. The spacer elements are spaced apart along lens to the support elements to provide a plurality of ventilation openings located between the support elements and the spacer elements. The one eyepiece lens is connected to the outer support element to retain the lens within the frame so that the ventilation openings are exposed between the lens and the wearer's face. The goggles retainer cooperates with the eyepiece frame to retain the frame against the wearer's face.

A detailed disclosure following, related to drawings, describes a preferred embodiment and an alternative of the invention, the invention being capable of expression in structure other than that particularly described and illustrated.

DETAILED DESCRIPTION

FIGS. 1 through 6

Figure 1:
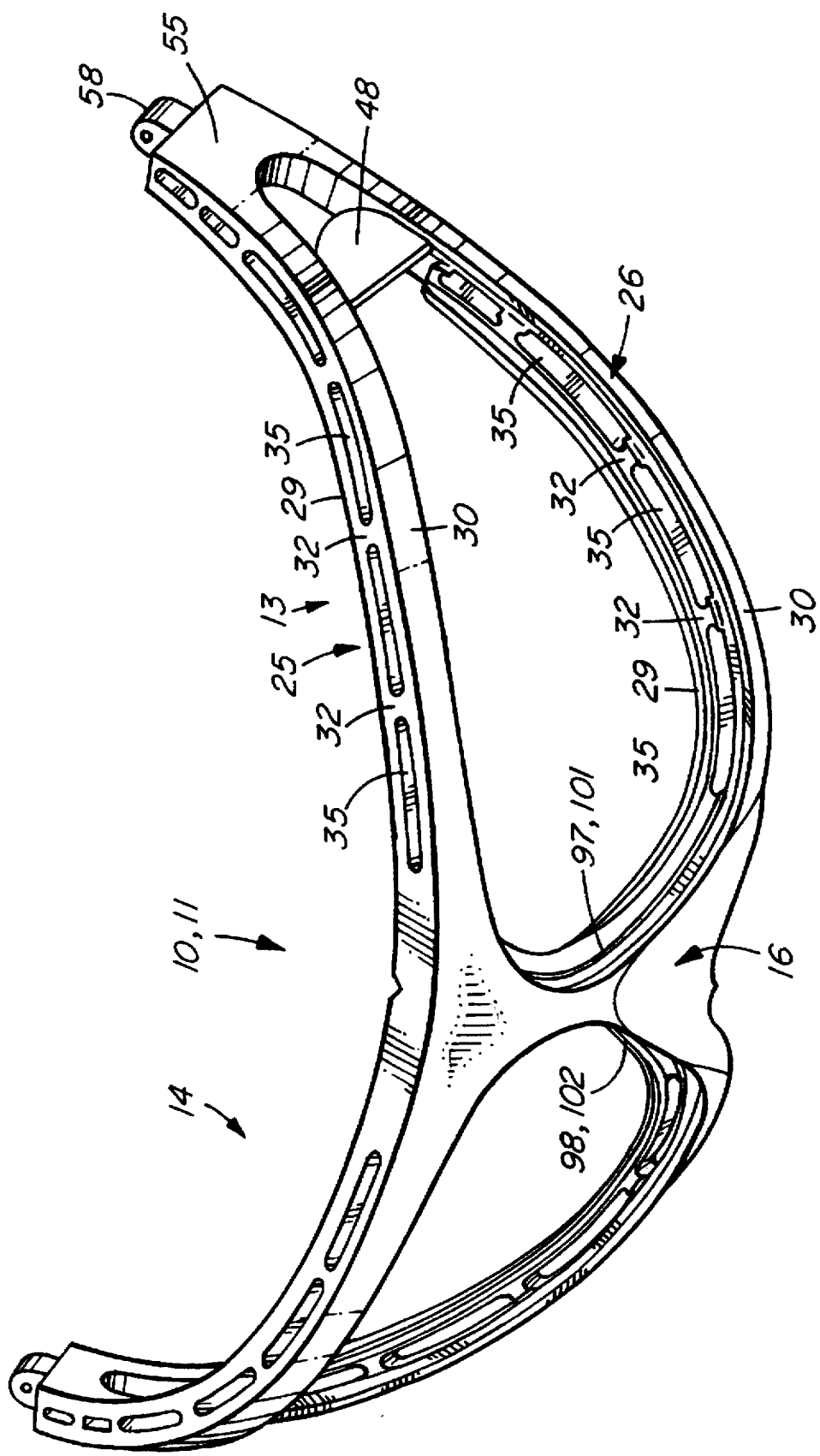
FIG. 1 is a simplified front perspective of an integrally moulded dual eyepiece goggles frame in accordance with the invention, with a goggles retainer, resilient items and eyepiece lenses removed for clarity.

Eye goggles 10 according to the invention comprise a one-piece or integral dual eyepiece goggles frame 11 having left and right eyepiece frames 13 and 14 connected together by a nosepiece 16. The frame is preferably molded in high impact Nylon (TM) to provide a high strength-to-weight ratio. The goggles further comprise separable left and right eyepiece lenses 19 and 20 fitted within the respective frames 13 and 14, and a goggles retainer 22 cooperating with the eyepiece frames to retain the goggles against the wearer's face as will be described. The eyepiece lens are preferably made of hard coated polycarbonate, and treated for filtering or reflecting harsh light and to reduce fogging from condensation. The eyepiece frames and lenses are mirror images of each other about an axis of symmetry 24, and thus, in general, the left hand frame and associated lens only will be described.

Figure 4:
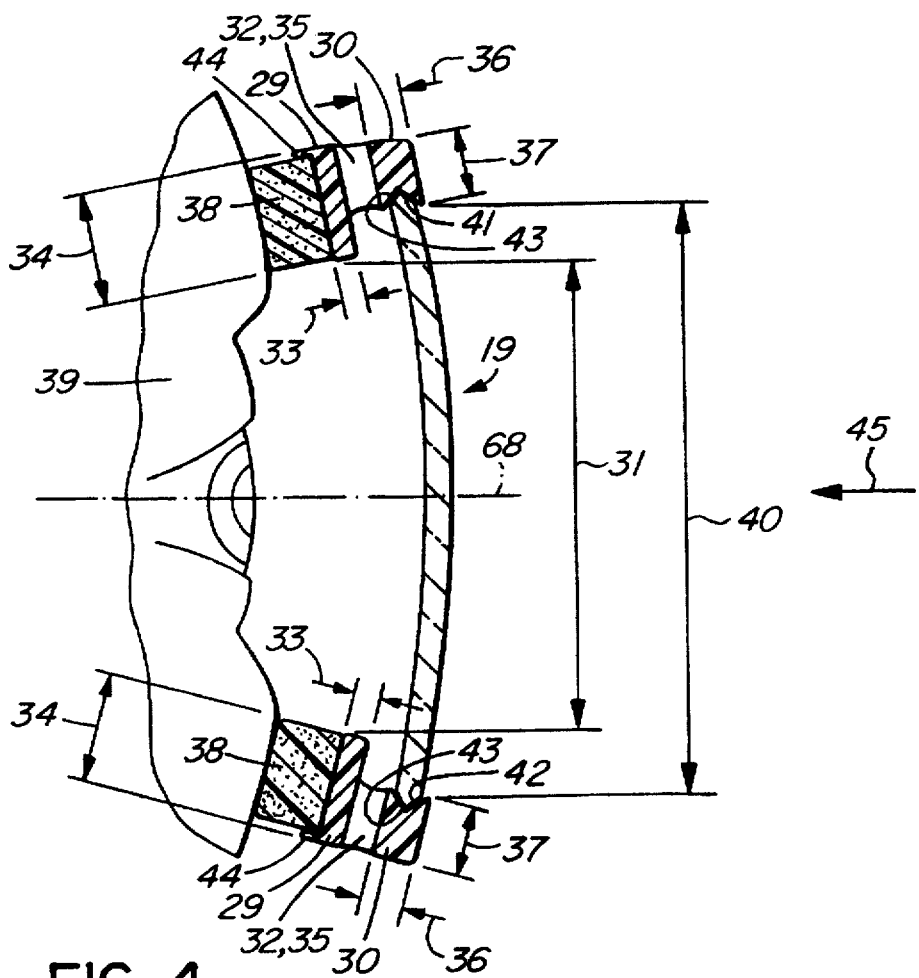
FIG. 4 is a simplified transverse section through the goggles, as seen generally on line 4—4 of FIG. 2, with a portion of the wearer's face shown for clarity.

As best seen in FIGS. 1 and 4, the left eyepiece frame 13 has upper and lower edge portions 25 and 26 comprising elongated and spaced apart inner and outer support elements 29 and 30 respectively. The support elements are spaced apart by a plurality of relatively short spacer elements 32, are generally parallel to each other and extend in generally similar directions and to define the upper and lower edge portions of the eyepiece frame. The spacer elements are spaced apart along the length of the support elements to provide a plurality of ventilation openings 35 located between the support elements and the spacer elements.

As best seen in FIG. 4, each inner support element 29 has a thickness 33 and a width 34, ratio of thickness to width being within a range of between approximately 1:10 and 1:15. In contrast, each outer support element 30 has a greater thickness 36 and a narrower width 37, and ratio of thickness to width is between approximately 1:1.5 and 1:2.

Also, outwardly facing outer edges of the inner and outer support elements are generally co-planar with each other so that the upper and lower edge portions 25 and 26 are pleasing in appearance and provide a relatively smooth band, provided with a row of elongated openings defining the ventilation openings. In contrast, inwardly facing inner edges of the inner support elements 29 extend inwardly much more than adjacent corresponding inwardly facing edges of the outer support elements. Thus, spacing 31 between the inner edges of the inner support elements 29 is considerably smaller than spacing 40 between inner edges of the outer support elements 30. This provides additional security for the wearer as it is essentially impossible for the lens 19 to pass easily inwardly between the inner support elements, and thus there is little chance of injury to the wearer's eye should the lens 19 be inadvertently separated from the outer support elements to which it is secured, as will be described.

It is noted that the thickness 33 of the inner element is less than the thickness 36 of the outer element, and ratio of the thickness 33 to the thickness 36 is between about 1:2 and 1:3. Thus, the inner element is slightly more flexible than the outer element to provide a measure of resilience, whereas the outer element is stiffer to provide additional strength for engaging the eyepiece lens as will be described. Preferably, a resilient padding 38 is bonded to and extends along the inner support elements so as to cushion the goggles adjacent a wearer's face 39 without materially obstructing airflow through the ventilation openings. Thus, the inner support elements 29 are locatable between the wearer's face and the outer support element. In addition, a small lip 44 extends from an outer edge of each inner support element 29 towards the wearer's face to protect the bond between the padding 38 and the element 29 by masking the bond line and increasing stability of the padding 38.

The eyepiece lens 19 is connected to the outer support elements 30 to retain the lens securely within the eyepiece frame 13, although preferably the lens should be relatively easy to remove from the frame to provide interchangeability of lenses for different lighting conditions. One means of providing easy interchangeability of lenses is to provide inwardly facing edges of the outer support elements 30 of the edge portions 25 and 26 with V-shaped grooves 41 and 42 respectively, in which each groove faces inwardly towards the opposite outer support element. The eyepiece lens has a generally V-shaped edge 43 extending therearound and being generally complementary to the V-shaped grooves 41 and 42 in the outer support elements 30 so as to be received snugly therein. The lens has a thickness of approximately 0.08 inches (2.0 mm) for safety reasons, and the thickness 36 of the outer support element 30 is preferably about twice the thickness of the lens and thus the support element 30 provides an anchor of adequate strength to retain the edges of the lens therein. It can be seen in FIGS. 1 and 4 that the ventilation openings are disposed between the lens and the wearer's face, and are located in two curved rows one above the other to provide a plurality of passages for convective cooling when the wearer's face is upright.

An important feature of the invention relates to the high strength of the goggles frame, which is necessary to withstand any impact sustained by the lens itself, as well as impacts on the frame. In contrast to other multi-sport glasses, the present frame is designed to be sufficiently stiff to withstand impact loads, while obtaining some support from the wearer's face. This is attained by providing a relatively stiff space frame of the inner and support elements which pass around the eye to provide a sturdy anchor to support edges of the eyepiece lens. The spacer elements are thus spaced apart pillars connecting the inner and outer support elements together, but holding them spaced apart to increase the modulus of cross-section. Each pair of inner and outer support elements and associated spacer elements thus provide a girder-like beam which is particularly adapted to sustain loads in a direction normal to the width or broader faces of the support elements. As best seen in FIG. 1, the inner and outer support elements providing the lower edge portion of each eyepiece frame merge into each other and extend upwardly and inwardly to form the nosepiece, so as to connect four of the lower support elements together at the nosepiece to improve strength.

The eyepiece lens 19 is partially spherical, is curved in two places, and extends convexly outwardly from the wearer's face. Thus, the lens is "dome-like" or "arched" to provide resistance to deflection if the lens is impacted generally normally to its surface. Any generally perpendicular force applied to the lens 19 in direction of an arrow 45 tends to flatten the lens, which in turn imposes an outwards lateral force on the outer support elements 30, i.e. generally perpendicularly to the arrow 45. The complementary V-shapes of the grooves 41 and 42 and the lens edge 43 tends to augment retention of the edges of the lens by the support elements thus reducing chances of the lens being inadvertently pushed into the eye. In addition, each outer support element 30 has a modulus of cross-section located to most effectively absorb outwards directed forces from the lens. Thus, the ratio of the thickness 36 to the width 37 enables the outer support element to withstand most forces resulting from load on the lens tending to flatten the lens.

Figure 2:
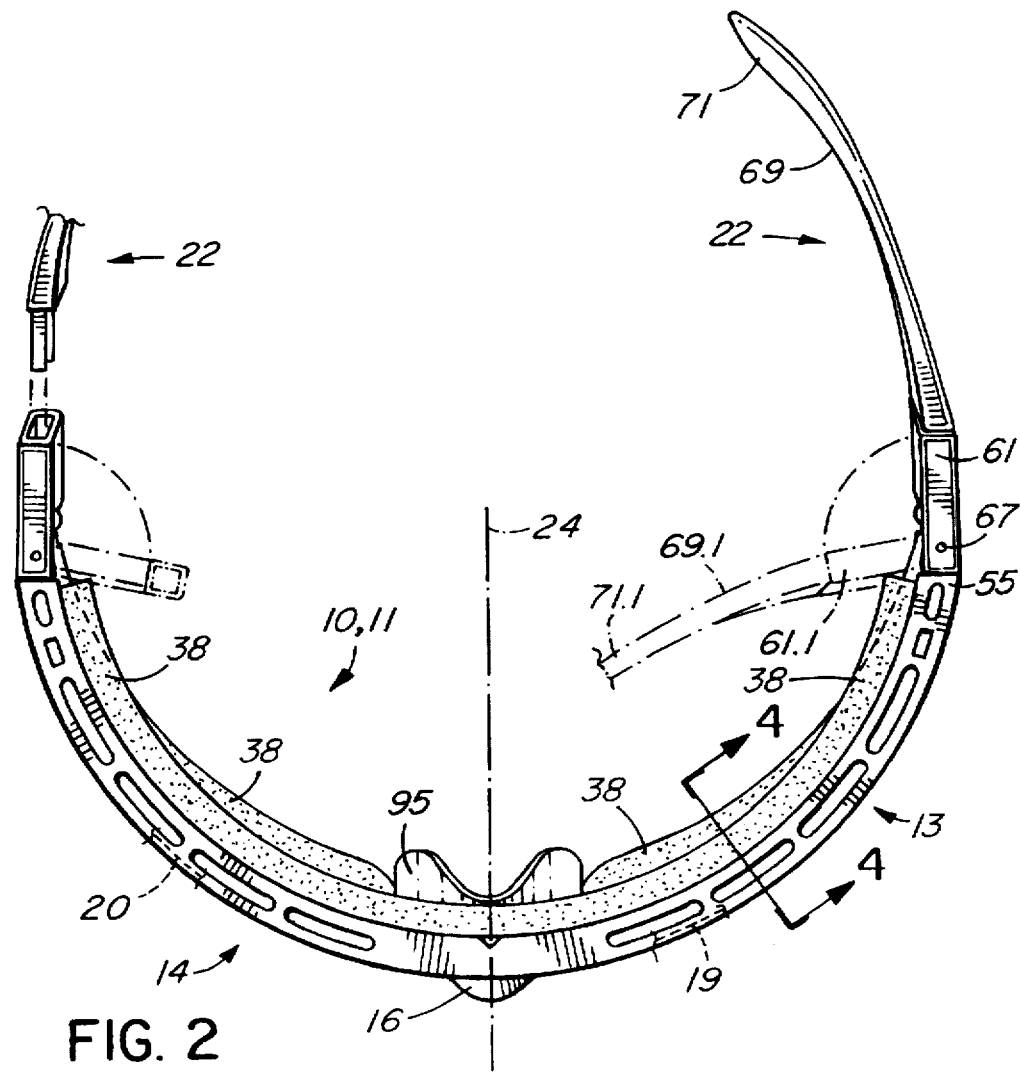
FIG. 2 is a simplified fragmented top plan view of the complete goggles, fitted with head engaging arms shown in extended and retracted positions.
Figure 5:
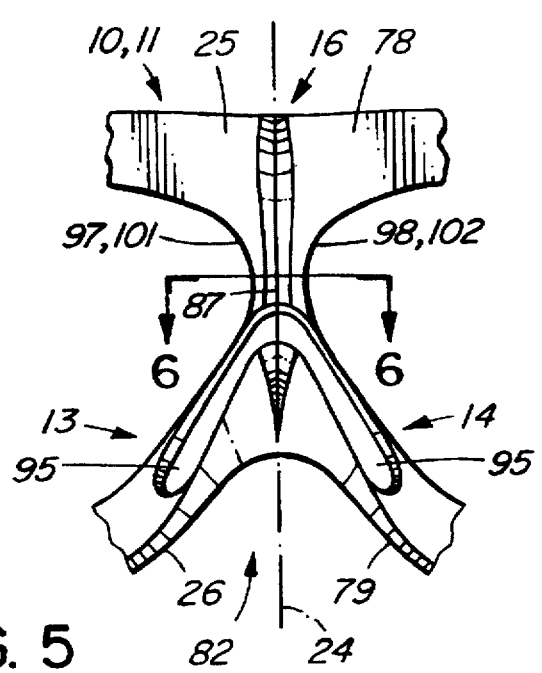
FIG. 5 is a simplified fragmented rear elevation of portions of the goggles adjacent the wearer's nose.
Figure 6:
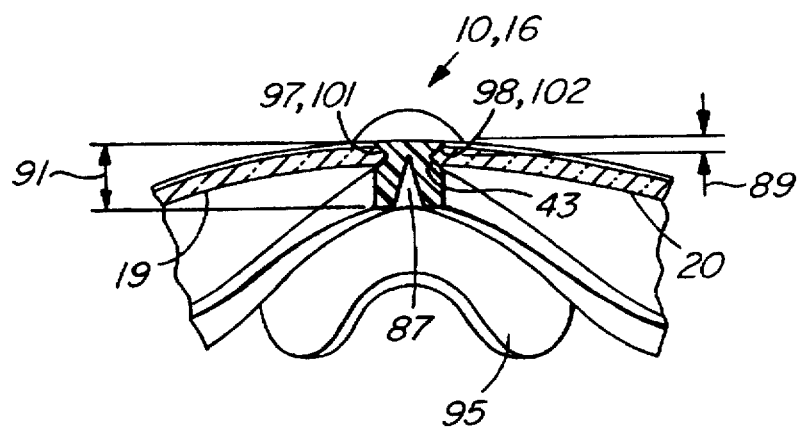
FIG. 6 is a simplified fragmented section on line 6—6 of FIG. 5.

As indicated earlier, it is essentially impossible for the lens 19 to pass laterally between the inner support elements 29 should an edge of the lens be forced out of the frame due to an impact. The resulting free edge of the lens would likely contact and be restrained by the adjacent inner support element 29 of the frame, and thus not move inwardly to injure the wearer's eye. In addition, the outer margin of the partially spherical lens has an outer surface generally parallel to outer surfaces of adjacent portions of the outer support elements so as provide a generally smooth exterior appearance and only a small step as a transition between the lens and support elements, thus reducing the possibility of a foreign object hitting the step and possibly damaging the goggles As best seen in FIG. 2, the eyepiece frame 13 is curved to conform as closely as possible to the wearer's face which also assists in providing a sturdy support for the lens. The eyepiece frames 13 and 14 are integrally interconnected at the nosepiece 16 which, as will be described with reference to FIGS. 5 and 6, provides a hinge of limited movement to accommodate variations between faces of most wearers. Clearly, resilience in the resilient padding 38 accommodates minor variations between faces as well as providing additional comfort for the wearer.

Figure 3:
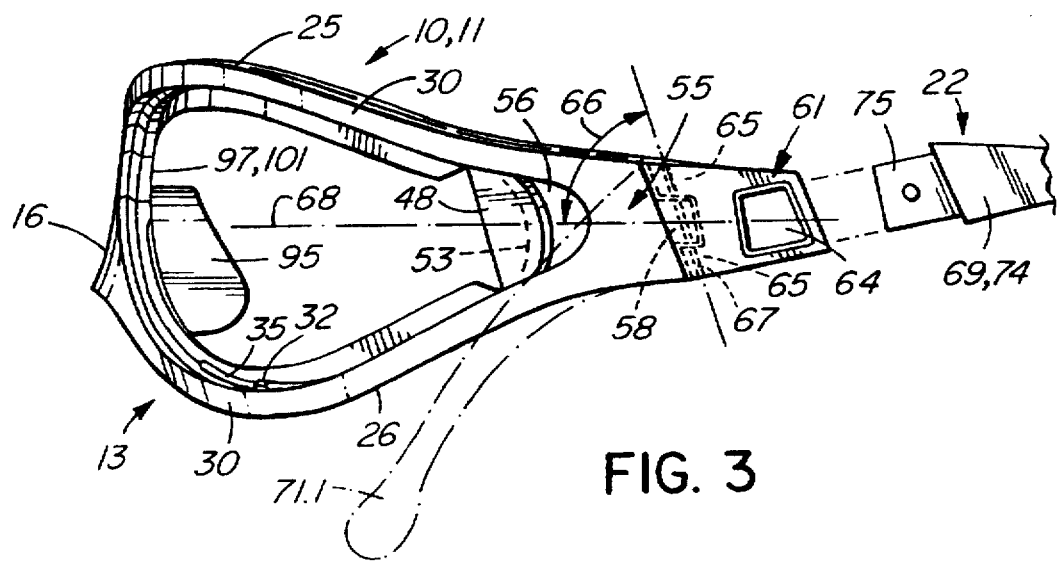
FIG. 3 is a simplified fragmented side elevation of the goggles of FIG. 2, with an eyepiece lens and portion the head engaging arm removed.

As best seen in FIGS. 1 and 3, the upper and lower edge portions 25 and 26 of the eyepiece frame 13 converge rearwardly towards each other on a side of the eyepiece frame remote from the nosepiece 16. A connector 48 extends between oppositely facing portions of the outer support elements 30 of the upper and lower edge portions 25 and 26 of the frame. The connector has an inwardly facing inner face, not shown, which contacts an adjacent portion of an outer face of the lens so as to retain an outer corner portion 53 (broken line in FIG. 3) of the eyepiece lens remote from the nosepiece. Thus, the edge of the lens adjacent the corner portion 53 is not retained in a V-shaped groove as elsewhere, but instead the lens face lies against the connector 48 and this provides space for sufficient movement of the lens to facilitate insertion and removal of the lens from the frame as will be described.

The upper and lower edge portions 25 and 26 are also interconnected at extreme positions remote from the nosepiece by a frame hinge portion 55 which is disposed rearwardly of the connector 48 to provide a rear ventilation opening 56 therebetween to enhance air flow through the goggles. However, in some conditions, e.g. water spray, it may be desirable to close the opening 56 by use of a removable, clip-on cover, not shown. The portion 55 is sufficiently sturdy and rigid to provide an anchor for the goggles retainer 22 which is connected to a goggles hinge, which comprises a frame hinge boss 58 extending rearwardly from the portion 55, the boss being shown exposed in FIG. 1 and in broken outline in FIG. 3. The goggles hinge also comprises an inner arm portion 61 having a pair of spaced arm hinge bosses 65 (broken outline in FIG. 3) which straddle the frame hinge boss 58. The bosses 58 and 65 have aligned openings to receive a hinge pin 67 passing therethrough so that the arm hinge portion is hinged to the adjacent frame hinge portion. This permits limited swinging of the portion 61 about the goggles hinge between an extended position as shown in full outline in FIG. 2, and a retracted position shown in broken outline and designated 61.1. The inner arm portion 61 is also a portion of the goggles retainer 22 and has an outer end having a latch portion 64 which has a recess to cooperate with a complementary tang of a latch portion as will be described.

As seen in FIGS. 2 and 3, the goggles retainer 22 further comprises an outer arm portion 69 having an outer end with a head engaging portion 71 which is shown in broken outline at 71.1 in the retracted position. The arm has an ear engaging hook which resembles the outer end of the conventional spectacle arms. The outer arm portion has an inner end 74 having a tang which serves as a latch portion 75 which is complementary to the latch portion 64 of the inner arm portion.

As seen in FIGS. 3 and 4, the hinge pin 67 is inclined at an angle 66 to a main optical plane of goggles 68, the main optical plane passing through an optical axis of the wearer's eye when the eye looks horizontally with the head upright. Thus, as the arm portion swings from the extended position to the retracted position, the arm portion sweeps through an arc disposed at right angles to the hinge pin 67, which results in portion 71 of the arm passing below the lenses to be clear of the lenses so as to prevent contact between the ends of the folded arms and the lenses. This prevents the ends of the arms damaging the lenses which is a common problem with many sunglasses where the hinge axis is disposed generally perpendicularly to the axial plane.

Figure 7:
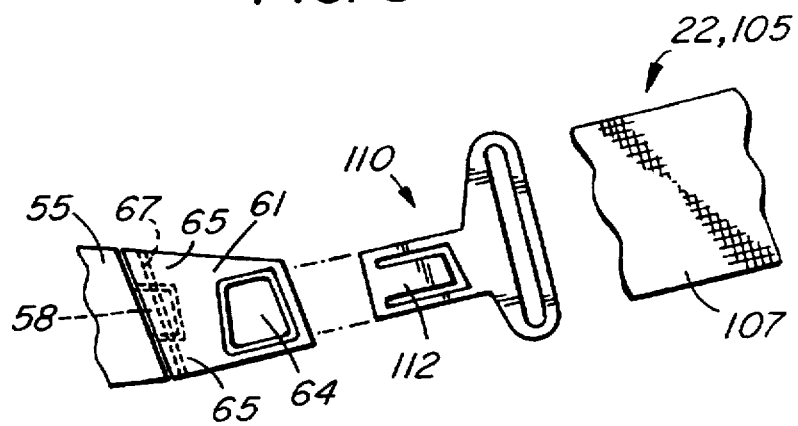
FIG. 7 is a simplified fragmented side view of a portion of an eyepiece frame and an inner arm portion hinged thereto, with a detachable head engaging portion or head band.
Figure 8:
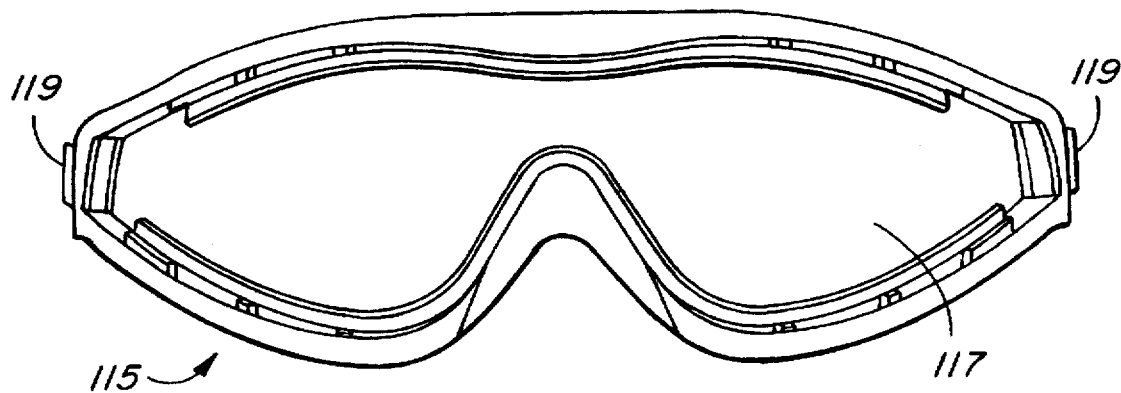
FIG. 8 is a simplified front elevation of an alternative single eyepiece goggles frame.

An alternative goggles retainer will be described with reference to FIG. 7.

As best seen in FIGS. 5 and 6, the eyepiece frame 14 has upper and lower edge portions 78 and 79 which resemble the corresponding edge portions 25 and 26 of the opposite eyepiece frame 13. The elongated support elements 29 and 30 providing the lower edge portions 26 and 79 of the eyepiece frames extend upwardly and inwardly towards each other to define a generally inverted V-shaped recess 82 below the nosepiece 16 and between the eyepiece frames 13 and 14 to receive the wearer's nose, not shown. The nosepiece 16 has a hinge portion 87 extending along the nosepiece and within the axis of symmetry 24. The hinge portion 87 is a relatively narrow central strip of the nosepiece having a reduced thickness 89 which is less than thickness 91 of surrounding portions to the goggles frame to provide a hinge portion of increased flexibility. The strip extends between upper edges of the eyepiece frames to an apex of the V-shaped recess 82 to facilitate limited bending between the eyepiece frames to accommodate variations in shapes and faces of different wearers.

As also seen partially in FIGS. 1 and 3, a inverted V-shaped resilient nose support 95 extends around the generally inverted V-shaped recess 82 between the eyepiece frames to provide a cushion for supporting the goggles upon the wearer's nose. The nosepiece 16 has an oppositely facing edge portions 97 and 98 provided with outwardly facing grooves 101 and 102 respectively which are aligned with and interconnect the upper and lower grooves 41 and 42 on the outer support elements 30 of the eyepiece frames. In this way, edges of the eyepiece lenses adjacent the nosepiece are retained within the V-shaped grooves of the nosepiece similarly to retention of the lens edges 43 within the edge portions 25 and 26 of the eyepiece frames. This ensures sturdy and accurate location of inner portions of the eyepiece lenses within the frames and further restricts deflection of the lenses under impact forces.

Operation

The goggles are worn in a variety of activities while retained on the head using the arm portions 69 as in conventional spectacles, or alternatively using a resilient head band as will be described with reference to FIG. 7. In contrast to prior art goggles, the lenses 19 and 20 can be easily interchanged by applying a force to the rear facing surface of the lens away from the eye, to displace the lens forwardly from the V-shaped grooves 41 and 42 following slight lateral outwards displacement of the edge portions 25 and 26. As described above, to essentially eliminate the risk of eye injury, it is very difficult to remove the lens by displacing the lens towards the eye. A lens is re-inserted into the frame by first placing the corner portion 53 of the lens inwardly of the connector 48, and gently spreading the edge portion 25 and 26 laterally outwardly to enable the edge 43 of the lens to be received easily in the V-shaped grooves 41 and 42 and the corresponding grooves in the edge portion of the nosepiece.

Alternatives

Preferably the goggles frame 11 is made as an integral unit, i.e. the eyepieces and the nosepiece are molded in one piece. Alternatively each eyepiece could be made an integral unit and interconnected at an alternative nosepiece by a conventional hinge providing limited hinging movement therebetween. In any event, the nosepiece extends continuously between the eyepiece flames to locate the frames sturdily relative to each other.

FIG. 7

The goggles retainer 22 has an alternative head band embodiment 105 having a resilient or elastic headband 107 adapted to pass around a portion of the wearer's head. The band has opposite end portions, which are preferably loops, not shown, which cooperate with a pair of band connectors 110, one band connector only being shown cooperating with the inner arm portion 61. The band connector has a tang providing a band latch portion 112 which is complementary to the recess of the latch portion 64 of the inner arm portion 61. In this way, if a wearer decides that a headband would be more appropriate than the outer arm portions 61 of FIGS. 1–4, the latch portions 75 of the outer arm portions are disconnected from the inner arm portions 61, and the band latch portions 112 are substituted. Clearly, use of the headband in most circumstances provides a more secure means of retaining the goggles on the wearer's head.

FIG. 8

The eye goggles 10 of the present invention has a dual eyepiece frame with distinctly separated left and right eyepiece frames and lenses. Separate lenses are preferred for many activities because the lens portions are necessarily smaller, and thus in general, stronger. In addition, the hinge in the nosepiece enables the frame 11 to conform to the shape of wearer's faces.

However, in some instances it may be preferred to have a single or unitary one-piece lens sufficiently large for both eyes. An alternative single eyepiece goggles frame 115 has a single eyepiece lens 117 retained within a single eyepiece frame which passes around both eyes in a manner somewhat similar to a conventional ski goggles mask. The frame has similar loops of generally parallel inner and outer support elements, interconnected by a plurality of shorter spacer elements in the manner similar to the dual eyepiece frames as illustrated. The eyepiece lens is curved in two planes and connected to the outer support element of the frame to retain the lens within the frame so that the ventilation openings are exposed between the lens and the wearer's face. A goggles retainer 119, preferably of the elastic headband type, has opposite ends connected to opposite sides of the frame in a manner similar to conventional ski goggles.

I claim:

1. Eye goggles comprising:
   (a) a goggles frame having a pair of eyepiece frames interconnected together by a nosepiece extending essentially continuously between the eyepiece frames to locate the eyepiece frames sturdily relative to each other, each eyepiece frame having upper and lower edge portions comprising elongated and spaced apart relatively stiff inner and outer support elements, the inner support elements being locatable between a wearer's face and an adjacent outer support element, the support elements being spaced apart by a plurality of relatively stiff and short spacer elements and being curved in generally similar directions to conform approximately to the wearer's face so as to obtain some support therefrom, the spacer elements being spaced relatively closely together along the support elements to provide a relatively stiff space frame with essentially uniform support of the outer support elements to resist deflection thereof, and to provide a row of ventilation openings located between the support elements and the spacer elements,
   (b) a pair of eyepiece lenses, each lens being connected to a respective outer support element of each eyepiece frame to retain the lens within the frame, so that the ventilation openings are exposed between the lens and the wearer's face, and (c) a goggles retainer cooperating with the eyepiece frames to retain the goggles against the wearer's face.

2. Eye goggles as claimed in claim 1, in which:

(a) each outer support element has a groove therein to receive an edge of the eyepiece lens.

3. Eye goggles as claimed in claim 1, in which:

(a) each outer support element has a thickness greater than the thickness of each inner support element to provide additional thickness for the groove to receive the eyepiece lens.

4. Eye goggles as claimed in claim 1, in which:

(a) each inner support element has a width greater than width of the outer support element to provide a greater beating area against the wearer's face, and (b) spacing between oppositely facing inner edges of the inner support elements is smaller than spacing between oppositely facing inner edges of the outer support elements to prevent the lens from passing through an opening defined by the inner support elements to provide additional safety for the wearer's eye.

5. Eye goggles as claimed in claim 1, in which:

(a) the nosepiece has a hinge portion extending therealong, the hinge portion being a relatively narrow strip having a thickness less than thickness of surrounding portions of the goggles frame and extending between the eyepiece frames to facilitate limited bending between the eyepiece frames to accommodate variations in shapes of faces of different wearers.

6. Eye goggles as claimed in claim 5, in which:

(a) the inner and outer support elements providing the lower edge portion of each eyepiece frame merge into each other and extend upwardly and inwardly towards the adjacent eyepiece frame to define a generally inverted V-shaped recess between the eyepiece frames to receive the wearer's nose, the recess having an apex generally adjacent the hinge portion.

7. Eye goggles as claimed in claim 6, further including:

(a) a resilient nose support extending around the generally inverted V-shaped recess between the eyepiece frames to provide a cushion for supporting the goggles upon the wearer's nose.

8. Eye goggles as claimed in claim 2, in which:

(a) the support elements providing the upper and lower edge portions of each eyepiece frame terminate generally adjacent the nosepiece, and (b) the nosepiece has opposed edge portions provided with outwardly facing grooves which are aligned with and interconnect the grooves on the outer support elements of the eyepiece frames so as to retain edges of the eyepiece lenses adjacent the nosepiece.

9. Eye goggles as claimed in claim 1, in which:

(a) the support elements providing the upper and lower edge portions of each eyepiece frame converge towards each other on a side of each eyepiece frame remote from the nosepiece, and (b) a connector extends between the upper and lower edge portions of each eyepiece frame, the connector having an inwardly facing inner face which contacts an adjacent portion of an outer face of the lens so as to retain an outer corner portion of the eyepiece lens remote from the nosepiece.

10. Eye goggles as claimed in claim 1, in which:

(a) the support elements providing the upper and lower edge portions of each eyepiece frame are interconnected at positions remote from the nosepiece to provide a frame hinge portion for each eyepiece frame remote from the nosepiece, and (b) the goggles retainer comprises a pair of inner arm portions, each inner arm portion having an arm hinge portion hinged to an adjacent frame hinge portion of each eyepiece frames, and a latch portion on a side of the inner arm portion remote from the arm hinge portion.

11. Eye goggles as claimed in claim 10, in which the goggles retainer further comprises:

(a) a pair of outer arm portions, each outer arm portion having an outer end with a head engaging portion, and an inner end having a latch portion complementary to the latch portion of the inner arm portion.

12. Eye goggles as claimed in claim 11, in which:

(a) the arm hinge portion is hinged to the frame hinge portion for rotation about a hinge axis which is inclined to a main plane of the goggles passing through the wearer's eyes, so that the head engaging portions of the outer arms are clear of the lenses when the outer arms are hinged to retracted positions.

13. Eye goggles as claimed in claim 10, in which the goggles retainer further comprises:

(a) a resilient head band adapted to pass around a portion of a wearer's head, the band having opposite end portion, and (b) a pair of band connectors, each band connector having a band latch portion complementary to the latch portions of the inner arm portions and being connected to the ends of the head band.

14. Eye goggles as claimed in claim 1, in which:

(a) the eyepiece lenses extend convexly outwardly from the wearer's face and have edges cooperating with respective outer support elements in such a way that any outwards forces imposed by the lens on the support element tend to augment retention of the edges of the lens by the support elements.

15. Eye goggles as claimed in claim 14, in which:

(a) the eyepiece lens is partially spherical.

16. Eye goggles as claimed in claim 15, in which:

(a) the partially spherical lens has an outer margin having an outer surface generally parallel to outer surfaces of adjacent portions of the outer support elements so as to provide a generally smooth exterior appearance.

17. Eye goggles as claimed in claim 1, further comprising:

(a) a resilient padding extending around the inner support elements so as to cushion the goggles adjacent the face without materially obstructing air flow through the ventilation openings.

18. Eye goggles as claimed in claim 1, in which:

(a) the goggles frame is moulded as a one-piece integral unit.

19. Eye goggles comprising:

(a) a goggles frame having a single eyepiece frame having upper and lower edge portions comprising elongated and spaced apart relatively stiff inner and outer support elements, the inner support element being locatable between a wearer's face and the outer support element, the support elements being spaced apart by a plurality of relatively stiff and short spacer elements, and being curved in generally similar directions to conform approximately to the wearer's face so as to obtain some support therefrom, the spacer elements being spaced relatively closely together along the support elements to provide a relatively stiff space frame with essentially uniform support of the outer support elements to resist deflection thereof, and to provide a row of ventilation openings located between the support elements and the spacer elements, (b) one eyepiece lens connected to the outer support element to retain the lens within the frame, so that the ventilation openings are exposed between the lens and the wearer's face, and (c) a goggles retainer cooperating with the eyepiece frame to retain the frame against the wearer's face.

20. Eye goggles as claimed in claim 19, in which:

(a) each outer support element has a groove therein to receive an edge of the eyepiece lens, and a thickness greater than thickness of the inner support element to provide additional width for the groove to receive the eyepiece lens, (b) each inner support element has a width greater than width of the outer support element to provide a greater bearing area against the wearer's face, and (c) spacing between oppositely facing inner edges of the inner support elements is smaller than spacing between oppositely facing inner edges of the outer support elements to prevent the lens from passing through an opening defined by the inner support elements to provide additional safety for the wearer's eyes.

\* \* \* \* \*